United States Patent [19]

Fischer

[11] Patent Number: 4,923,458
[45] Date of Patent: May 8, 1990

[54] SURGICAL FIXATION PIN TENSION ADJUSTER

[75] Inventor: David A. Fischer, Edina, Minn.

[73] Assignee: Ace Medical Company, Los Angeles, Calif.

[21] Appl. No.: 853,140

[22] Filed: Apr. 17, 1986

[51] Int. Cl.$^5$ .............................................. A61F 5/04
[52] U.S. Cl. ........................................ 606/59; 606/57
[58] Field of Search ........ 128/92 ZW, 92 YE, 92 YS, 128/92 Z, 92 ZZ, 92 ZY, 92 R, 84 B; 403/22, 118, 355; 254/98, 100; 74/89.15, 424.8 R; 606/54–59

[56] References Cited

U.S. PATENT DOCUMENTS

| | | | |
|---|---|---|---|
| 2,035,952 | 3/1936 | Ettinger | 128/84 B |
| 2,250,417 | 7/1939 | Ettinger | 128/92 Z |
| 2,401,757 | 6/1946 | Hardsolg | 74/424.8 R |
| 2,432,695 | 12/1947 | Speas | 128/92 ZW |
| 4,006,740 | 2/1977 | Volkov et al. | 128/92 Z |
| 4,078,440 | 3/1978 | Dalton et al. | 74/89.15 |
| 4,290,344 | 9/1981 | Adams | 74/89.15 |

FOREIGN PATENT DOCUMENTS

| | | | |
|---|---|---|---|
| 0596750 | 3/1978 | U.S.S.R. | 403/355 |
| 1128940 | 12/1984 | U.S.S.R. | 128/92 Z |

Primary Examiner—Stephen C. Pellegrino
Assistant Examiner—Ralph Lewis
Attorney, Agent, or Firm—Grant L. Hubbard

[57] ABSTRACT

A tension adjuster is mounted on and is part of an external fixation device comprising frame segments rigidly supporting fixation pins that pass through and immobilize fractured bones during rehabilitation. This tension adjuster securely attaches the fixation pins to the frame segments and adjustably applies tension along the fixation pins to more rigidly secure the fixation pins and to improve the immobilization of the fractured bones. The tension adjuster comprises a threaded slotted screw attached to the fixation pins and comprises a mounting nut having an aperture through which is drawn the threaded slotted tension screw while adjusting the tension along the fixation pins. A tapered pin extending into the aperture of the mounting nut and into a chamfered slot of the threaded slotted tension screw, guides the threaded slotted tension screw through the mounting nut during tension adjustments. A tension nut rotating upon the threaded slotted tension screw and buttressing the tension mounting nut operates by simple turning motion to draw the threaded slotted tension screw through the tension mounting nut and thereby applying tension along the fixation pins.

2 Claims, 2 Drawing Sheets

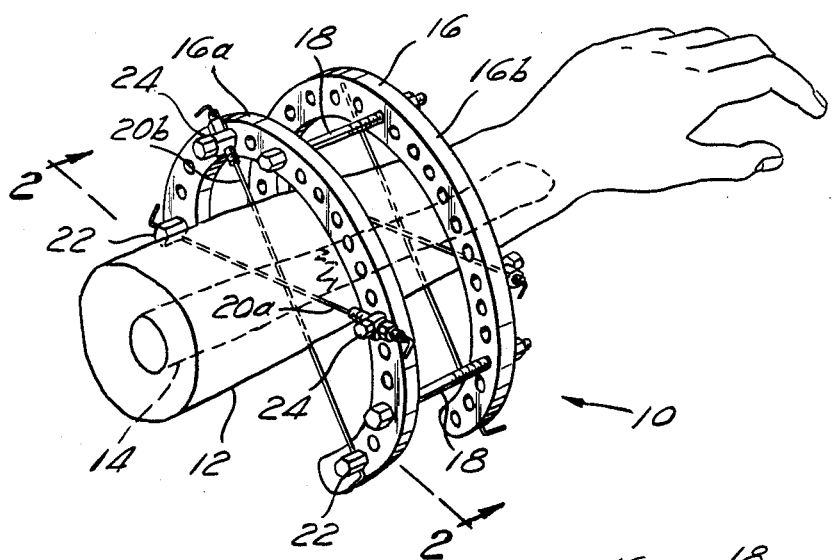
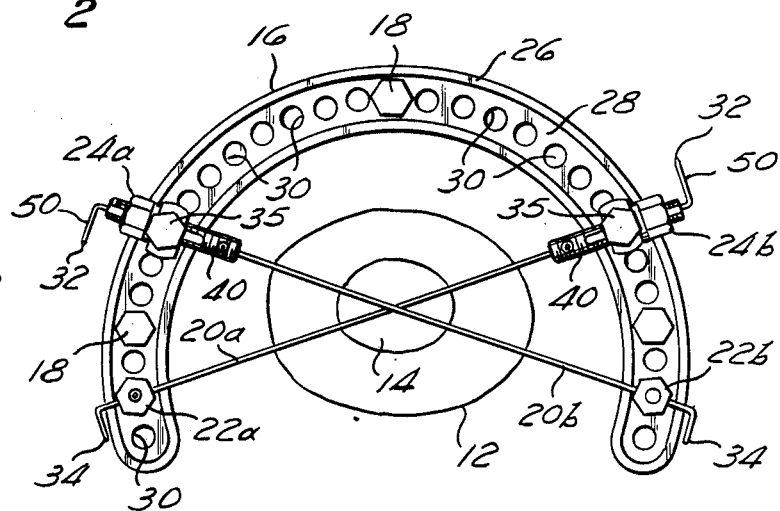
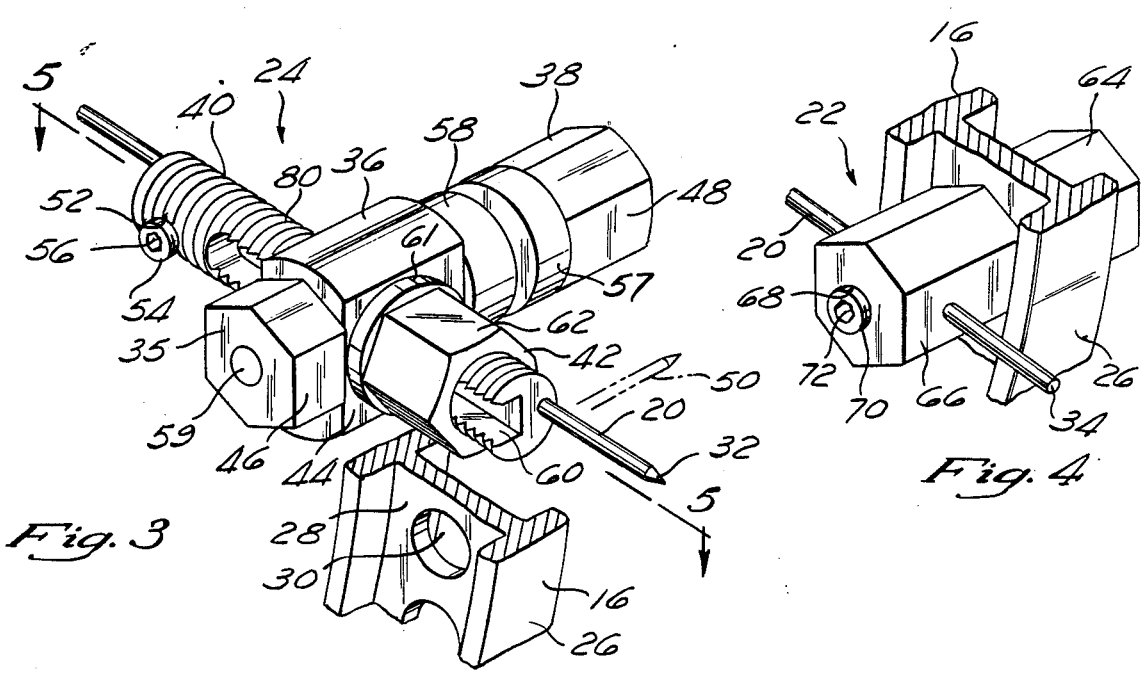

SURGICAL FIXATION PIN TENSION ADJUSTER

BACKGROUND

The present invention relates to orthopedic medical apparatus and more particularly to medical apparatus used to treat fractured bones which are repositioned and immobilized by fixation means external to the soft body tissue. Such medical apparatus are referred to very broadly as external fixation devices. The present invention relates directly to fastening means which hold surgical fixation pins in fixation frame structures, which fastening means are also used to apply tension to the fixation pins penetrating the fractured bones so as to more securely position and immobilize the fractured bones.

External fixation has long been recognized as a viable means of treating bone fractures. A recent new external fixation device is described in U.S. Pat. No. 4,450,834 issued May 29, 1984 to David A. Fischer which patent is here incorporated by reference as there fully set forth. The external fixation device disclosed in U.S. Pat. No. 4,450,834 comprises a pair of arcuate frame seegments which cooperate together as well as with a plurality of surgical fixation pins secured and mounted to the arcuate frame segments. The invention therein disclosed also comprises pin holders which were positioned at various locations upon the arcuate frame segment. The holders secured the surgical fixation pins to the arcuate frame segments so as to securely position the fractured bone, through which, pass the surgical fixation pins.

There, the pin holders of the claimed invention have an elongated body which includes a plurality of horizontal apertures which extend through the width of the body. Each aperture is sized to loosely receive a convention surgical fixation pin. The elongated body also includes a plurality of rectangular vertical pockets formed perpendicularly to the horizontal apertures. The pockets extend from an upper surface of the pin holder and terminate at some distance below the horizontal apertures but above the lower surface of the elongated body. Each of the vertical pockets are sized to slidely receive a pin lock member having a rectangular shaped body and a threaded stud. The body of the pin lock member includes a central aperture also for losely receiving a fixation pin.

In operation, the pin lock is losely vertically inserted down into one of the pockets formed in the elongated body. A surgical fixation pin is horizontally inserted through the aperture formed in the elongated body as well as the horizontal aperture formed in the pin lock. Subsequently, an acorn fastener is threadedly mounted onto the stud causing the pin lock to be pulled tightly downward against the surgical fixation pin thereby accurately centering the pin within the pin holder and securely locking the fixation pin into position by the concentric forces exerted along the contact surface between the outer diameter of the surgical fixation pin and the aperture surfaces of both the elongated body and the pin lock.

The pin holders do not provide for a tension force upon the surgical fixation pin along its length for rigidly holding the fixation pin thereby enabling limited bowing of the fixation pin. Hence, the surgical fixation device disclosed in the prior art patent lacks suitable means for applying tension to the surgical fixation pin preventing bowing. This inability to apply tension along the length of the surgical fixation pins permits movement of the fractured bone positioned and secured by the external fixation device. Such movement of the fractured bone may delay the healing process or may cause the fractured bones to heal incorrectly requiring further surgery or resulting in permanent disfigurement of the bone.

The surgeon needs to operate quickly and efficiently so as to minimize incorrect healing processes prior to correct fixation of the fractured bone in the external fixation device. Thus, another disadvantage with the pin holder of the prior art patent is the complex structure of the pin holder which is difficulty manipulated during surgical operations addressing fractured bones.

During operations, the surgeon must place a plurality of pin locks through apertures in the elongated body of the pin holder. These pin locks are small and have the corresponding small apertures which require the utmost dexterity of the surgeon during the surgical operation. From time to time, such lock pins may be dropped or otherwise mishandled during the surgical process. These and other disadvantages are solved or minimized using a surgical fixation pin tension adjuster of an external fixation device.

SUMMARY

An object of the present invention is to provide a tension adjuster of an external fixation device which adjuster enables tension to be applied along the length of surgical fixation pins.

Another object of the present invention is to provide an external fixation device with fixation adjusters which are easily manipulated during surgical operations.

A tension adjuster is attached along the length of arcuate frame segments of the fixation device. The tension adjuster secures one end of a surgical fixation pin. The other end of the fixation pin is connected to another securing means which is also attached along the length of the arcuate frame segments. The securing means secures the fixation pin respecting a point along the arcuate frame segment. Thus, the surgical fixation pin is securely attached along the length of the arcuate frame segments at two different locations. The tension adjuster is suitably adapted to apply tension to the surgical fixation pin so as to more rigidly fix the fixation pin and correspondingly more rigidly position and immobilize a fractured bone.

The tension adjuster is also suitably adapted to enable surgeons to conveniently and easily manipulate the tension adjuster by simple screw action during the operation.

The tension adjuster comprises a tension mounting nut which is rigidly attached to the arcuate frame segment along the length thereof. A body portion of the tension mounting nut has a circular aperture in which is disposed a tapered pin extending from the circumference of the circular aperture toward but not reaching its center. The circular aperture and tapered pin are suitably adapted to receive a threaded slotted tension screw.

One end of the surgical fixation pin has a sharp pointed end for bone and soft tissue penetration. The pointed end of the fixation pin passes completely through and is securely fastened to the threaded slotted tension screw having a slot extending from one end closest to the pointed end of the fixation pin toward but not reaching the other end of the threaded slotted tension screw.

The tapered pin in the circular aperture of the body portion of the tension adjuster extends into the slot of the threaded slotted tension screw and thereby positions the threaded slotted tension screw in the circular aperture. A tension nut is screwed onto the threaded slotted tension screw and buttresses the body portion of the tension mounting nut. As the tension nut is turned, the threaded slotted tension screw moves through the circular aperture of the body portion of the tension mounting nut.

While the tension nut is turned upon the threaded slotted tension screw and while the tension screw buttresses the body portion of the tension mounting nut, the threaded slotted tension screw moves through the body portion of the tension mounting nut thereby applying tension upon the surgical fixation pin by virtue of the attachment of the threaded slotted tension screw to the surgical fixation pin. The tapered pin extending into the circular aperture and into slot of the threaded slotted tension screw is particularly adapted so as to conveniently align the threaded slotted tension screw in the circular apearture and particular adapted to enable the threaded slotted screw to conveniently slidably move through the circular aperture.

The tension adjuster is characterized by easy assembly and manipulation during adjustments. The body portion and tension nut of the tension adjuster apply tension to the surgical fixation pin by simple screw movement of the tension nut. These and other advantages will become more apparent in the following description of the preferred embodiment.

DRAWING DESCRIPTIONS

FIG. 1 depicts an external fixation device attached to a fractured bone so as to immobolize the fractured bone during rehabilitation.

FIG. 2 is a frontal view of an arcuate frame segment with two surgical fixation pins attached thereto which pins pass through a patient's arm.

FIG. 3 is a perspective view of a tension adjuster.

FIG. 4 is a perspective view of a securing means.

PREFERRED EMBODIMENT

Figure 5:
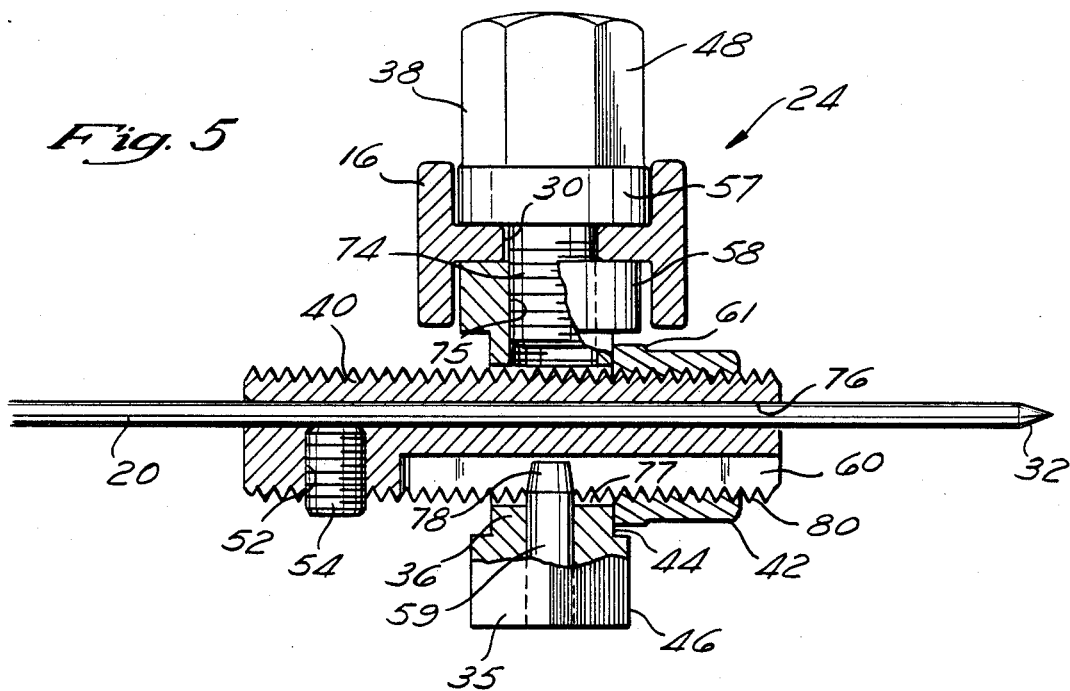
FIG. 5 is a cross-sectional diagram of the tension adjuster.

Referring to FIG. 1, an external fixation device 10 is disposed about a patient's arm 12 having a fractured bone 14. The external fixation device 10 comprises two arcuate frame segments 16a and 16b positioned in parallel. The arcuate frame segments 16 are displaced from each other by a plurality of threaded bolts 18.

Referring to FIGS. 1 and 2, two surgical fixation pins 20a and 20b are securely attached to the arcuate frame segments 16 by use of securing means 22a and 22b and tension adjusters 24a and 24b. The arcuate frame segment 16 has a flange portion 26 and a web portion 28. The web portion 28 has a plurality of circular mounting apertures 30. These apertures 30 are used for receiving either securing means 22, tension adjusters 24 or threaded bolts 18.

The securing means 22 and tension adjusters 24 position portions of the fractured bone 14 respecting the arcuate frame segments 16. After penetration through the fractured bone 14 by the fixation pins 20 and after attachment of the fixation pins 20, to the frame segment 16, the threaded bolts 18 guide the arcuate frame segments 16 toward each other by screw action as the differing portions of fractured bone 14 are brought together. Hence, the arcuate frame segments 16 guide differing portions of a fractured bone toward each other while positioning the differing portions of the fractured bone 14 in an immobile, fixed and anatomical correct alignment for proper healing.

Typically, each of the surgical fixation pins 20 has a pointed end 32 extending through a respective tension adjuster 24. The pointed end 32 of the surgical fixation pin 20 is used to pierce soft body tissue and portions of the fractured bone 14 while reducing trauma thereto. Each of the surgical fixation pins 20 also have a respective blunt end 34 extending through a respective securing means 22. Both the pointed end 32 and the blunted end 34 of the surgical fixation pin 20 may be bent after the surgical fixation so as to prevent possible injury by ends 32 or 34 to the patient.

Referring to FIG. 3, a tension adjuster 24 comprises a tension mounting nut 35, a tension mounting screw 38, a threaded slotted tension screw 40 and a tension nut 42. The tension mounting nut 35 has a body portion 36 having a flat surface 44 for receiving in a buttress relation the tension screw 40. The tension mounting nut 35 also has flat portion 46, and the tension mounting screw 38 has another flat portion 48. The two flat portions 46 and 48 are hexagonal in shape suitably adapted to receive wrenches (not shown) for securely fastening together the tension mounting nut 35 and the tension mounting screw 38 onto arcuate frame segments 16.

The surgical fixation pin 20 is inserted through the threaded slotted tension screw 40 parallel to the longitudinal axis of the threaded slotted tension screw 40 but not coincident therewith. The pointed end 32 extends beyond the end of the threaded slotted tension screw 40. A bent portion 50 of the fixation pin 20 is bent perpendicular to the longitudinal axis of the threaded slotted tension screw 40 as a safety precaution and to prevent the threaded slotted tension screw 40 from sliding along the fixation pin 20.

A threaded securing aperture 52 of the threaded slotted tension screw 40 extends from the circumference of the threaded slotted tension screw 40 to the fixation pin 20 disposed therein. A threaded securing screw 54 has threads suitably adapted for screwing the threaded securing screw 54 into the threaded securing aperture 52. The threaded securing screw 54 is screwed into the threaded slotted tension screw 40 so as to buttress against and clamp the threaded slotted tension screw 40 securely to the fixation pin 20 disposed therein. Hence, the threaded slotted tension screw 40 is rigidly clamped to the fixation pin 20.

The threaded securing screw 54 has a hexagonal aperture 56 located at an exposed end thereof, which hexagonal aperture 56 is used in cooperation with a wrench (not shown) having a head portion which is hexagonal and which fits into the hexagonal aperture 56. Commonly known ALLEN wrenches are especially suitable for manipulating the threaded securing screw 54 by virture of a hexagonal head portion especially sized to fit within the hexagonal aperture 56 and suitably adapted to impart rotation to the threaded securing screw 54.

The arcuate frame segment 16 extends and is disposed between a curved portion 57 of the tension mounting screw 38 and another curved portion 58 of the tension mounting nut 35. A bolt (not shown) of the tension mounting screw 48 extends through the mounting aperture 30 so as to securely position the tension adjuster 24 along the length of the arcuate frame segment 16.

The body portion 36 of the tension adjuster 24 has a circular aperture (not shown) therethrough having a diameter slightly larger than the major diameter of the threaded slotted tension screw 40 so as to permit the threaded slotted tension screw 40 to be slidably inserted into and drawn through the body portion 36.

The integrative tension mounting nut 35 which comprises the hexagonal flat portion 46, the body portion 36 and the curved portion 58 also includes a tapered pin 59. The tapered pin 59 extends from the top surface of the hexagonal flat portion 46 into the body portion 36 and further extends into the circular aperture (not shown) of the body portion 36. The tapered pin 59 also extends into a slot 60 of the threaded slotted tension screw 40 when the screw 40 is positioned within the circular aperture of the body portion 36.

An extending end (not shown) of the tapered pin 59 is disposed in the circular aperture of the body portion 36 such that as the threaded slotted tension screw 40 is passed through the circular aperture of the body portion 36, the threaded slotted tension screw 40 is aligned therein by placement of the tapered pin 59 into slot 60, thereby preventing rotation of the threaded slotted tension screw 40 about its longitudinal axis within the circular aperture of the body portion 36.

The tension nut 42 has a curved portion 61 which buttresses up against the flat surface 44 of the body portion 36. The tension nut 42 also has hexagonal flat portion 62 suitably adapted for manipulation by wrenches (not shown) so as to screw the tension nut 42 around and along said threaded slotted tension screw 40.

When the curved portion 61 buttresses against the flat surface 44 and when screw action of the tension nut 42 continues, the threaded slotted tension screw 40 is drawn through the circular aperture of the body portion 36. As the threaded slotted tension screw 40 is drawn through the body portion 36, the surgical fixation pin 20 is simultaneously drawn therethrough because of the attachment between the fixation pin 20 and the threaded slotted tension screw 40. Thus, tension is applied to the surgical fixation pin 20 by simple screw action upon the tension nut 42. Moreover, the threaded slotted tension screw 40 is easily aligned within the body portion 36 by the extension of the tapered pin 59 into the slot 60.

Referring to FIG. 4, the arcuate frame segment 16 supports the securing means 22 comprising a securing mounting screw 64 and a securing mounting nut 66. Both the securing mounting nut 66 and securing mounting screw 64 have hexagonal flat surfaces suitably adapted for receiving wrenches imparting rotation. The securing mounting screw 64 has a bore with threads therein (not shown) into which extends a threaded bolt (not shown) extending from the securing mounting screw 64. The securing mounting nut 66 is typically held stationary while the securing mounting screw 64 is rotated into the securing mounting nut 66 thereby clamping together the securing mounting nut 66 and the securing mounting screw 64 to the arcuate frame segment 16.

A threaded securing aperture 68 having threads (not shown) therein is suitably adapted for receiving a threaded securing screw 70 having a hexagonal aperture 72 at an exposed end thereof. The hexagonal aperture 72 is similar to the hexagonal aperture 56 in that they both are especially suitably adapted for receiving ALLEN wrenches. The threaded securing screw 70 buttresses the surgical fixation pin 20 within the securing mounting nut 66 thereby clamping and rigidly securing the fixation pin 20 to the securing mounting nut 66.

Referring to FIGS. 3 and 4, both the securing means 22 and the tension adjuster 24 receive a respective end 34 and 32 of the surgical fixation pin 20. The securing means 22 and the tension adjuster 24 are used for rigidly securing the fixation pin 20 about the arcuate frame segment 16. The tension adjuster 24 is also used to apply a tension force upon the fixation pin 20 along its length so as to more rigidly fix the fixation pin 20 without bowing between the securing mounting means 22 and the tension adjuster 24.

Figure 6:
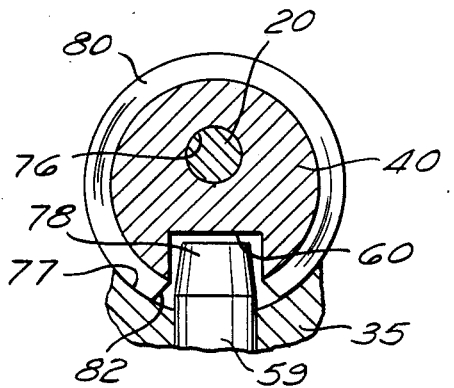
FIG. 6 is another cross-sectional view showing a tapered pin inserted into a threaded slotted tension screw.

Referring to FIGS. 5 and 6, the tension mounting screw 38 has a threaded bolt portion 74 which extends through the circular mounting aperture 30 and is screwed into a threaded bore 75 within the curved portion 58. The bolt portion 74 is integral with the tension mounting screw 38 and is used to position the tension adjuster 24 along the length of the arcuate frame 16.

The fixation pin 20 is slidably inserted through a pin cavity 76 within the threaded slotted tension screw 40 in parallel to but not coincident with the longitudinal axis of threaded slotted tension screw 40. The threaded securing screw 54 is used to clamp the fixation pin 20 into the threaded slotted tension screw 40. The tension slot 60 runs along the longitudinal length of the tension screw 40 on its circumference from an end closest to the pointed end 32 of fixation pin 20 to near the threaded securing screw 54.

The design of tapered pin 59 and the slot 60 combine providing easy insertion, alignment and slidability of the threaded tension screw 40 through the circular aperture 77 of the tension mounting nut 35. The tapered pin 59 has a tapered end 78 extending into the slot 60 thereby aligning the tension screw 40 into the tension mounting nut 35.

The diameter of the tapered pin 59 is slightly less than the thickness of the slot 59. The tapered end 78 extends into the slot but does not touch the bottom of the slot such that the tapered end 78 has some freedom of movement within the slot 60 permitting the tension screw 40 to easily slide along and through the body portion 36 of the tension mounting nut 38.

To further improve the slidability of the tension screw 40 through the tension mounting nut 35 while providing alignment of the mounting screw 40 by virture of the tapered pin 59 being inserted into the slot 60, threads 80 of the tension screw 40 have a chamfer 82 at approximately 45°. This chamfer 82 minimizes friction between the tapered end 78 and the slot 60 while reducing debris formation by making the upper edges of the slot in the screw substantially linear, thus resulting in a substantially point-to-point contact between frustoconically tapered portion 78 of the guide pin 59 and the edges of the slot 60, all as shown in FIG. 6.

INDUSTRIAL APPLICATION

This invention is used in the field of orthopedic surgery, primarily. It should now become apparent that the tension nut 42 is the single action means for applying tension to the fixation pin 20 after the apparatus is in place. During a surgical operation, a surgeon may manually tighten the tension adjuster 24 possibly followed by post operative tightening by wrenches. It should also become readily apparent that the slot 60 easily slides about the tapered pin 59 having a certain degree of freedom therein.

Even though modifications and differing designs of the tension adjusters, tapered pins and slots modifications and differing designs may be invented and conceived by those skilled in the art, those modifications and designs may nevertheless represent applications and principles within the spirit and scope of the present invention as defined by the following claims.

What is claimed is:

1. In a tension adjuster in an external fixation device having a frame segment and a surgical fixation pin secured at the respective ends thereof to the frame segment, the fixation pin passing through and immobilizing fractured bone during rehabilitation, the fixation pin being secured at one end along the length of said frame segment by a threaded slotted tension screw having a slot circumferentially disposed and extending parallel to its longitudinal axis and a tension mounting nut having an aperture for receiving the threaded slotted tension screw and comprising an alignment pin extending into the aperture of the mounting nut and into the slot of said threaded slotted tension screw to guide the threaded slotted tension screw, and a tension nut for receiving the tension screw and applying tension thereto: the improvement wherein: the threads of the tension screw adjacent the slot therein are chamfered to provide a substantially linear edge on the slot, and the alignment pin is frusto-conical in configuration, tapering from a larger proximal portion adjacent the periphery of the tension screw to a smaller distal portion interiorly of the slot in the tension screw, the slot and the alignment pin being so constructed and configured relative to each other that there is a substantially point contact between the surface of the tapered alignment pin and the edge of the slot in the tension screw.

2. The tension adjuster of claim 1 wherein the tension mounting nut is attached to said frame segment.

* * * * *